US006267756B1

(12) United States Patent
Feuerstein et al.

(10) Patent No.: US 6,267,756 B1
(45) Date of Patent: Jul. 31, 2001

(54) APPARATUS FOR THE OBSERVATION AND THE TREATMENT OF THE EYE USING A LASER

(75) Inventors: Manfred Feuerstein, Wachenheim; Ulrich Klingbeil, München; Herbert Langosch, München; Werner Reis, München; Karl-Heinz Wilms, Emmering; Wolfgang Eisenträger, Munich; Werner Bisle; Andreas Plesch, both of München, all of (DE)

(73) Assignee: G. Rodenstock Instrumente GmbH, Munich (DE)

( * ) Notice: Subject to any disclaimer, the term of this patent is extended or adjusted under 35 U.S.C. 154(b) by 0 days.

(21) Appl. No.: 08/208,901

(22) Filed: Mar. 11, 1994

Related U.S. Application Data

(62) Continuation of application No. 08/004,649, filed on Jan. 14, 1993, now abandoned, which is a continuation of application No. 07/711,387, filed on Jun. 6, 1991, now abandoned, which is a continuation of application No. 07/569,769, filed on Aug. 22, 1990, now abandoned, which is a continuation of application No. 07/445,933, filed on Dec. 5, 1989, now abandoned, which is a continuation of application No. 07/318,438, filed on Mar. 2, 1989, now abandoned, which is a continuation of application No. 07/127,896, filed as application No. PCT/DE87/00103 on Mar. 9, 1987, now abandoned.

(30) Foreign Application Priority Data

Mar. 8, 1986 (DE) .................................... 3607721
Nov. 8, 1986 (DE) .................................... 3638226

(51) Int. Cl.⁷ ...................................................... A61L 5/02
(52) U.S. Cl. .................................. 606/10; 606/4; 606/11; 606/13
(58) Field of Search ............................... 606/4–6, 10–12; 607/88, 89; 351/206–208, 215

(56) References Cited

U.S. PATENT DOCUMENTS

| 4,213,678 | * | 7/1980  | Pomerantzelf et al. | 351/206   |
| 4,266,549 | * | 5/1981  | Kimura              | 128/303.1 |
| 4,579,430 | * | 4/1986  | Bills               | 606/4     |
| 4,654,701 | * | 3/1987  | Yabe                | 128/4     |
| 4,669,466 | * | 6/1987  | L'Esperance         | 128/303.1 |
| 4,672,963 | * | 6/1987  | Barker              | 128/303.1 |
| 4,719,912 | * | 1/1988  | Weinberg            | 128/303.1 |
| 4,721,379 | * | 1/1988  | L'Esperance         | 128/303.1 |

FOREIGN PATENT DOCUMENTS

| 3024169 | * | 1/1982 | (DE) | 128/303.1 |
| 3148748 | * | 7/1983 | (DE) | 128/303.1 |
| 3425975 | * | 1/1986 | (DE) | 351/206   |
| 8705205 | * | 9/1987 | (WO) | 128/303.1 |

OTHER PUBLICATIONS

Awo Abstracts vol. 38, Summary 92.*

* cited by examiner

*Primary Examiner*—David M. Shay
(74) *Attorney, Agent, or Firm*—Antonelli, Terry, Stout & Kraus, LLP

(57) ABSTRACT

An apparatus for the observation and treatment of the eye with a laser, having an illumination light source, whose light is focussed on the part of the eye to be observed and which preferably contains a laser, a scanning device, which generates a scanning movement of the light of the illumination light source on the background of the eye, a detector device, which receives the reflected light, an evaluation and synchronization unit, which generates from the time-sequential signal output of the detector device a visual representation of the portions of the eye to be treated and shows the visual representation, on a monitor, and a treatment laser device, whose light can be reflected on the part of the eye to be treated. The apparatus provides that a visual representation in which the location or locations to be treated are marked, can be superimposed on the visual representation of the eye at least on the monitor, and a control unit aligns the laser to the marked location.

7 Claims, 1 Drawing Sheet

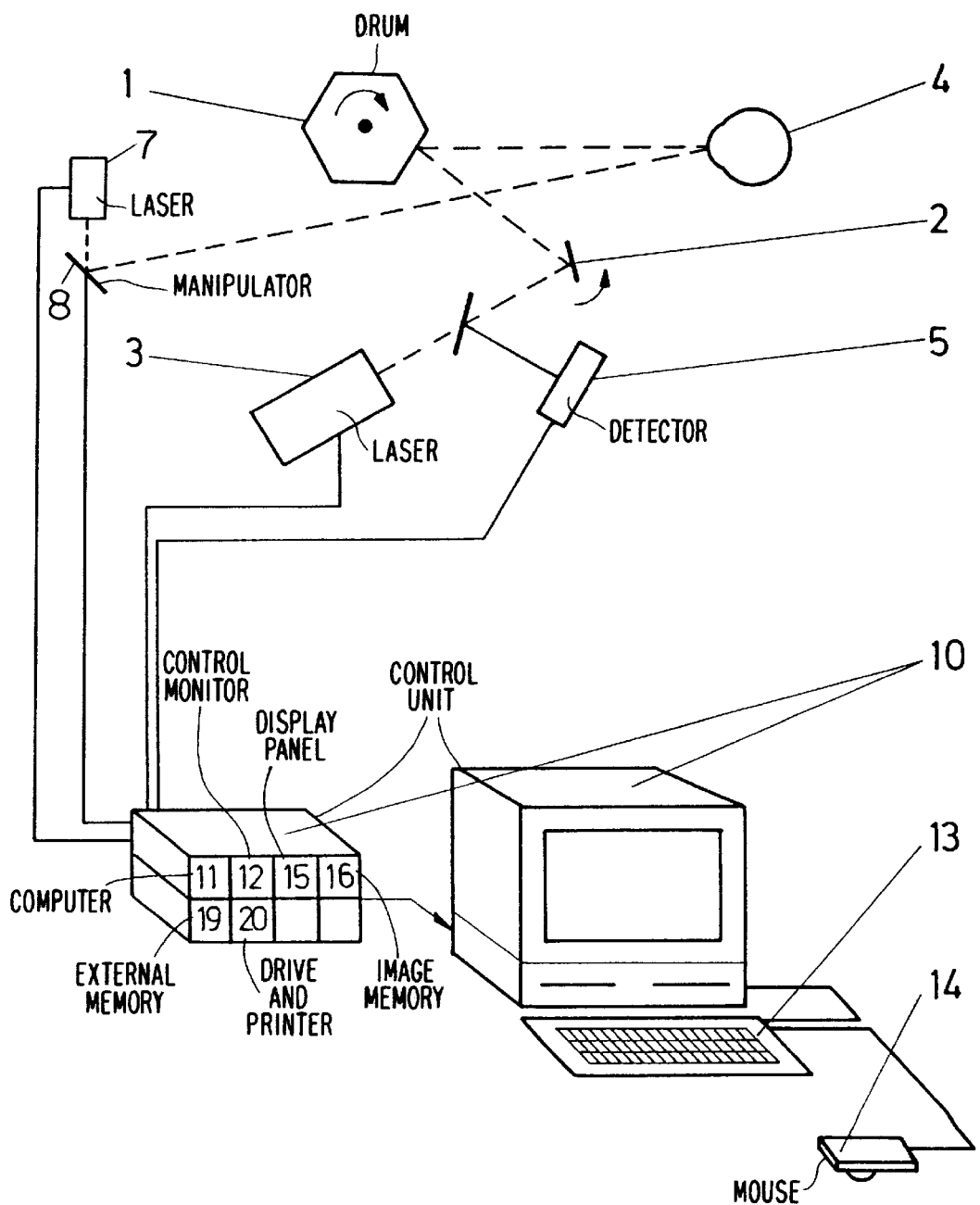

APPARATUS FOR THE OBSERVATION AND THE TREATMENT OF THE EYE USING A LASER

This application is a continuation of application Ser. No. 08/004,649, filed Jan. 14, 1993, now abandoned, which is a continuation of application Ser. No. 07/711,387, filed Jun. 6, 1991, now abandoned, which is a continuation of application Ser. No. 07/569,769, filed Aug. 22, 1990, now abandoned, which is a continuation of application Ser. No. 07/445,933, filed Dec. 5, 1989, now abandoned which is a continuation of application Ser. No. 07/318,438, filed Mar. 2, 1989, now abandoned, which is a continuation of application Ser. No. 07/127,896, filed Nov. 6, 1987, now abandoned which is a 371 of PCT/DE87/00103, filed Mar. 9, 1987.

BACKGROUND OF THE INVENTION

The present invention relates to an apparatus for the observation and the treatment of the eye using a laser.

State of the Art

By way of illustration, the observation of the rear portion of the eye poses the problem that the illumination and the observation must be conducted through the pupil of the eye and the often optically turbid front eye mediae, where reflexes occur and which cause aberration errors.

For this reason, it has often been suggested not to illuminate large areas of the background of the eye, but to scan as small as possible a spot with a focussed light and to detect the reflected light in ratio to the scanning sequence. In this connection, reference is made, by way of illustration, to "The Foundations of Ophthalmology", vol. VII, p. 307, 308, 1962, the U.S. Pat. No. 4,213,678 and the Japanese Patent Publications 61-5730 and 50-138822.

The apparatuses known from the above-cited references differ, e.g. in pupil separation: a "GULLSTRAND pupil" is suggested in the Japanese Patent Publication 61-5730 for the illumination and observation light, in U.S. Pat. No. 4,213, 678 it is an inverted "GULLSTRAND pupil" and in the Japanese Patent Publication 50 138822 it is adjacent pupils.

Furthermore, an apparatus for the observation of the rear portion of the eye is described in EP-A-O 145 563. In the apparatus the illumination and the observation light beam are directed via a scanning device. Such a "double scanning system" has the advantage that the reflected light beam can be demonstrated with a stationary detector having a relatively small surface.

The good image quality, that these known apparatuses deliver, predestine these apparatuses also for use in the treatment of the eye using a laser, as has already been suggested in U.S. Pat. No. 4,213,678.

Nonetheless these apparatuses could not gain ground as treatment devices for the following reasons:

The operator does not only have to refind the location to be treated, but also adjust the laser when the eye moves. These operations, which are also required with other laser treatment apparatuses, are, however, made more difficult with the prior described apparatuses due to the fact that the visual representation displayed on the monitor is monochrome and, thus, unaccustomed for the ophthalmologist, as the eye is illuminated by the light of the laser. Therewith the identification of the structures is made more difficult.

On the other hand, an apparatus of another type has been suggested in DE-OS 34 25 975, which provides a projection device, which, in particular, projects an angiograph of the eye to be treated in the path of the observation beam.

However, with the apparatus known from DE-OS 34 25 975 the operator must also not only make the projected visual representation concur with the image actually seen of the eye to be treated, but also constantly "adjusts" the laser, when the eye of the subject moves a little. Facilitated is only the identification of the location to be treated.

It is quite understandable that said two operations—adjusting the path of the obervation beam, by way of illustration of a slit lamp in order to make the angiograph concur with the visual representation of the fundus, adjusting the laser to the coagulation location—put a great strain on the operator. Such a strain can, under circumstances, lead to operation errors and thus to unfavorable treatment results.

Furthermore, an apparatus employing an indirect ophthalmoscope has been suggested, which is provided with a control unit which adjusts the laser beam to the movements of the eye (ARVO-Abstracts, vol. 38, Summary No. 92). The known apparatus is provided with an image processing unit, which analyzes the visual representation delivered during the treatment by an image indicating device. The adjustment ensues in the known apparatus in such a manner that the operator can select a well-defined area, by way of illustration a branching blood vessel and the control unit adjusts the laser beam in such a manner that the distance ratio of the location to be treated to the well-defined area remains constant during the treatment. The reason for this method of approach is that the present image processing sing units, which are realizable at cost prices affordable for ophthalmologist practices are not able, by way of illustration, to analyze the entire background of the eye in "real-time", as would be necessary in order to realize the adjustment while taking the entire indicated area into consideration.

The known apparatus, however, does not take into consideration that "morphologically" similar areas can occur in a human eye within the scope of the analysis of a typical image processing unit, by way of illustration branching blood vessels. In the event of rapid eye movement, it is therefore possible that the control unit indicates another "morphologically similar" branching blood vessel as the area initially selected and erroneously identifies this area as the area to which the distance ratio is to be held constant. In such a case, the control unit will align the laser to a different area than the area to be treated. It is not necessary to go into further detail that unacceptable damage to the eye can occur with the known apparatus.

DESCRIPTION OF THE PRESENT INVENTION

The object of the present invention is to improve an apparatus for observation and treatment of the eye using a laser in such a manner that facilitates the operation, on the one hand, and, on the other, excludes sources of errors due to erroneous alignment of the laser.

According to the present invention it has been recognized that one source of error in laser treatment and, in particular in the case of laser coagulation, is that the operator is, for a number of reasons, under pressure of time during the treatment when he mistakes an area, which is similar in structure, for the location to be treated, which he is supposed to find again by means of specific structures. According to the present invention, it has, therefore, been provided that a visual representation, on which the location or locations to be treated are marked, is superimposed upon the visual representation recorded by the detector device. By means of these markings, errors, by way of illustration caused by erroneous identification of structures, can be avoided.

As additional aid for the operator, the control unit prepositions the laser beam in such a manner that it is focussed on the marked location.

A combination of these features makes it possible for the treating ophthalmologist to draw up an operation plan at his leisure prior to the actual commencement of the treatment by seeking the locations to be treated, by way of illustration the locations to be coagulated, on a visual representation of the eye to be treated and marking it. During that part of the treatment when the patient is sitting in the operating chair and, during which, experience has shown, it is necessary to act quickly, the control unit provided in accordance with the present invention pre-positions the laser beam for the ophthalmologist so that the ophthalmologist only has to satisfy himself that the pre-positioning is good, perhaps make necessary corrections and subsequently release the laser beam.

On the other hand, by means of the invented combination of features the operator, i.e. the treating ophthalmologist, can check the quality of the positioning of the laser beam at any time by means of the visual representaton additionally superimposed upon the monitor, which, by way of illustration, shows the entire background of the eye. As the operator can check the concurrence of the superimposed visual representation with the actual image of the eye over a large area, "laser misses", which occur when two similar-looking areas have mistakenly been made to concur, cannot happen. Notwithstanding, the invented apparatus requires only a little computation, as by way of illustration not the entire, very strongly structured background of the eye has to be checked, but only the laser beam has to be adjusted to a marking.

Naturally, it is also possible to additionally align the laser beam manually in such a manner that the ophthalmologist continues to have freedom of choice during the treatment.

Thus, with the invented apparatus, it is possible to relieve the ophthalmologist of time-consuming processes and processes which often can only be performed inexactly manually, without relieving him of his professional responsiblity during actual treatment.

The invented apparatus can be employed in an advantageous manner in the treatment of the fundus as well as in the treatment of the front portion of the eye, such as the corneas, and is suitable for use with treatment lasers of all wavelengths operating in the visible, in the ultraviolet or in the infrared range. It is also possible to work with a separate target laser.

The output signals from the detector can, however, be fed into an image processing device and in this manner trigger various control or regulating processes: By way of illustration, the control unit can adjust the pre-positioned, superimposed visual representation, which the operator has made to concur with the actual image, for example the fundus, when the eye moves. In this way, the operator only has to adjust the path of the observation beam at the beginning of the treatment in such a manner that the path of the observation beam concurs with the taken visual representation. By this means the operation is further simplified, as the operator only has to take care at the beginning of the treatment that the projected visual representation is made to concur with the actual image of the eye:

The adjustment can occur in the manner as described, by way of illustration, in the afore-cited reference ARVOAbstracts. Nonetheless, the invented apparatus has the advantage that the ophthalmologist immediately recognizes, on the basis of the projected visual representation, when the control unit identifies a false location as the reference area; thus the ophthalmologist is able to switch the apparatus off or make corrections.

It is particularly advantageous if the location to be treated is marked by means of image processing on the superimposed video visual representaton with video visual representations this can be easily be accomplished with an appropriate image processing input device. Furthermore, the video visual representation can readily be adjusted on the monitor, by way of illustration, by means of hardware or software scrolling and adapted in size without requiring mechanically shifting the optical elements.

The control unit provided in accordance with the present invention has a memory, in which the treatment parameters, such as location of the coagulation or the cut in the cornea, laser beam output power, firing distance, etc. can be stored. Such storing of the treatment parameters permits not only consistant documentation, but also the scientific and/or legal evaluation of the treatment processes conducted with the invented apparatus.

In this connection, it is, at any rate, advantageous if the control unit is provided with an output device, by way of illustration a record printer, with which the required and the actual treatment parameters are read out.

Particularly advantageous is if the parameters prescribed for the treatment as well as the actual treatment parameters are identifiable on the monitor whereas it is especially advantageous if the parameters are correlated to the respective marking.

The control unit can also be employed to perform various safety functions:

It provided that the invented control unit interrupts the treatment when the projected visual representation no longer sufficiently concurs with that of the eye.

The laser beam can also be turned off when the white discoloring of the fundus has reached a certain level.

BRIEF DESCRIPTION OF THE DRAWING

The present invention is made more apparent in the following description of a preferred embodiment of the invention wherein the cole figure shows a schematic view of the invented apparatus.

DESCRIPTION OF A PREFERRED EMBODIMENT OF THE INVENTION

The present apparatus is provided in a prior art manner with a laser scanning ophthalmoscope having a scanning device, which preferably is composed of an x,y-scanner with a polygon mirror drum (1) and a galvanometer mirror (2) as such a system operates independently of wavelengths, which is an advantage when light of several wavelengths is employed simultaneously.

The scanning device directs the beam of a laser (3) to an eye (4), which is to be examined and treated, in such a manner that the laser beam scans the area to be treated. The light reflected by the eye is directed via the scanning device to a detector device (5), whose time sequential output signals are fed synchronically to the scanning movement by an electronic control and evaluation unit of prior art construction, to a video monitor on which in this manner a visual representation of the eye becomes visible.

The control unit (10), which is only depicted schematically, is provided with a computer (11) suitable for image processing, a control monitor (12), a keyboard (13), which can be provided possibly with a mouse input (14), a display panel (15), an image memory unit (16), an image sensor, which detects the eye to be treated, and an image monitor as well as an external memory (19), by way of illustration a diskette drive and a printer (20). The control unit (10) not only regulates the power and the firing time of laser (7), but also the laser beam's point of impact in the eye via a beam manipulator (8) in such a manner that the laser beam concurs with a marking provided in the projected visual representation. Furthermore, the control unit (10) adjusts the projected visual representation, which the operator has made to concur with that of the eye, when the eye to be examined moves. Moreover, said control unit permits the manipulation of a visual representation which was previously recorded by the invented apparatus or by another examining device prior to the actual treatment. In this manner, by way of illustration, the head ophthalomogist can plan the treatment—coagulation or cutting location, the laser power output etc.—but leave the actual treatment to an assistant.

The present invention is described afore using a preferred embodiment. Naturally, a great number of different modifications are possible within the scope of the overall inventive idea.

The control unit can also take over the regulation of other units, e.g. it can regulate the laser power output in accordance with the algorithms described in DE-OS 30 24 169 or DE-OS 33 06 981.

Particularly advantageous is, in any case, if the beam of the coagulation laser, thus by way of illustration of an AR⁺-laser or a color laser, is projected between the scanning device and the eye. Of course, it is also possible to raise the power of an obsrvation laser "briefly" for coagulating as described in U.S. Pat. No. 4,213,678. The joint use of the "scanning device" permits, particularly in this case, treating a larger area or several areas in one step.

An apparatus for the observation of the rear portion of the eye with a scanning illumination is particularly predestined as an image generator for a so-called eye tracking unit due to its reflex-free and high-analyzing image representation.

What is claimed is:

1. An apparatus for the observation and treatment of an eye with a laser, comprising:

an illumination light source including a laser for focusing laser light on a part of the eye to be observed;

a scanning unit generating scanning movement of the light of the illumination light source on the part of the eye to be observed;

a detector receiving scanning light reflected from the eye and providing a time-sequential output signal in accordance with detected reflected light;

an evaluation and synchronization unit responsive to the time-sequential output signal of the detector for generating a first visual image of the part of the eye to be observed;

a monitor for receiving the generated first visual image and for display thereof;

a treatment laser unit providing treatment laser light onto a part of the eye to be treated; and a controller including an image processing unit for generating a second visual image of the eye having markings thereon at least at one location on the eye to be treated so as to be superimposed on the first visual image of the eye on the monitor displaying the first visual image, the controller includes a deflector for deflecting the treatment laser light onto the eye;

wherein an operator manually superimposes the second visual image flush with the first visual image so as to be aligned therewith, and the controller continuously controls realignment of the superimposed images and of the treatment laser light with respect to the eye when the eye moves during treatment of the eye so as to enable the treatment laser light to impinge on the eye according to the marked location of the second visual image in accordance with the output signal of the detector unit.

2. An apparatus according to claim 1, wherein the controller includes means for detecting white discoloring of a coagulant.

3. An apparatus according to claim 1, wherein the controller includes means for regulating a power output of the treatment laser unit.

4. An apparatus according to claim 1, wherein the controller includes a memory for storing parameters for the treatment of the eye.

5. An apparatus according to claim 4, wherein the controller includes an output unit for controlling realignment of the treatment laser light.

6. An apparatus according to claim 4, wherein the memory includes means for storing at least one of required and actual treatment parameters.

7. An apparatus according to claim 6, wherein the controller includes means for displaying on the monitor at least one of the required and actual treatment parameters.

* * * * *